(12) United States Patent
Schwalm et al.

(10) Patent No.: US 7,488,856 B2
(45) Date of Patent: Feb. 10, 2009

(54) COMPOUNDS BASED ON FLUORANTHENE AND USE THEREOF

(75) Inventors: Reinhold Schwalm, Wachenheim (DE); Yvonne Heischkel, Mannheim (DE); Andreas Fechtenkoetter, Ludwigshafen (DE); Joachim Roesch, Ludwigshafen (DE); Florian Doetz, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 181 days.

(21) Appl. No.: 10/571,557

(22) PCT Filed: Sep. 9, 2004

(86) PCT No.: PCT/EP2004/010065

§ 371 (c)(1),
(2), (4) Date: Mar. 10, 2006

(87) PCT Pub. No.: WO2005/026088

PCT Pub. Date: Mar. 24, 2005

(65) Prior Publication Data

US 2007/0063189 A1 Mar. 22, 2007

(30) Foreign Application Priority Data

Sep. 11, 2003 (DE) ................. 103 42 340

(51) Int. Cl.
*C07C 13/66* (2006.01)
*C07C 25/22* (2006.01)
*C07C 205/06* (2006.01)
*C07D 333/08* (2006.01)
*C09K 11/06* (2006.01)
*H05B 33/14* (2006.01)

(52) U.S. Cl. .................. 570/129; 549/29; 549/41; 549/59; 257/E51.022; 257/E51.018

(58) Field of Classification Search .................. None
See application file for complete search history.

(56) References Cited

U.S. PATENT DOCUMENTS

| | | | |
|---|---|---|---|
| 3,190,887 A | 6/1965 | Hensley et al. | |
| 5,281,489 A | 1/1994 | Mori et al. | |
| 5,965,746 A | 10/1999 | Fujita et al. | |
| 2002/0022151 A1 | 2/2002 | Ishikawa et al. | |

FOREIGN PATENT DOCUMENTS

| | | |
|---|---|---|
| DE | 21 66 862 | 4/1976 |
| EP | 1 138 745 | 10/2001 |
| EP | 1 345 477 | 9/2003 |
| WO | 03/105538 | 12/2003 |

OTHER PUBLICATIONS

Laali, Kenneth K. et al., "Stable ion and electrophilic chemistry of fluoranthene-PAHs", J. Chem. Soc., Perkin Trans., vol. 2, No. 3, pp. 621-629, 2002.

Curtze, Juergen et al., "The synthesis of fluoranthenes and related aromatic polycycles by means of pyridinium salts", Chemische Berichte, vol. 112, No. 6, pp. 2197-2208, 1979. (with English abstract).

Zhukhovitskii, V.B., et al., "Haloacyl derivatives of polycyclic hydrocarbons. V. Condensations using haloacylfluoranthenes", Voprosy Khimii I Khimicheskoi Tekhnologii, vol. 30, pp. 27-31, 1973. (with English abstract).

Shenbor, M.I, "Fluoranthenyl-4-acetic acid and its derivatives", Zhurnal Organicheskoi Khimii, vol. 6, No. 5, pp. 1079-1081, 1970. (English abstract).

Davies, Alun et al., "The Nitration of Indeno [1,2,3-cd] fluoranthene", Journal of the Chemical Society, No. 11, pp. 1337-1339, 1968.

Buu-Hoie, N.P. et al., "Friedel-Crafts acylation reactions of polycyclic aromatic hydrocarbons. V. Acetylation of fluoranthene", Bulletin de la Societe Chimique de France, vol. 3, pp. 981-984, 1968. (with English abstrac).

Clar, E. et al., The location of double bonds in fluoranthene perylene and 1, 1'-dinaphthyl by NMR, Tetrahedron, vol. 25, pp. 5639-5648, 1969.

Praefcke, K. et al., :Eine ungewoehnliche bildung des Fluoranthen-Ringsystems, Tetrahedron Letters, No. 21, pp. 1787-1788, 1976.

Buu-Hoie, N.P. et al., "Carcinogenic Nitrogen Compounds. Part XL. [1] Condensed Heterocyclic Derivatives of Fluoranthene.", J. Chem. Soc., pp. 3920-3924, 1964.

(Continued)

*Primary Examiner*—Yvonne Eyler
*Assistant Examiner*—Yevgeny Valenrod
(74) *Attorney, Agent, or Firm*—Oblon, Spivak, McClelland, Maier & Neustadt, P.C.

(57) ABSTRACT

The invention relates to fluoranthene derivatives of the general formula (I)

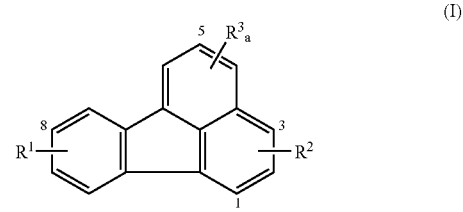

in which $R^1$, $R^2$, $R^3$ and a are each defined according to the description, with the proviso that at least one of the $R^1$ or $R^2$ radicals is not hydrogen, to processes for their preparation and to the use of the fluoranthene derivatives as emitter molecules in organic light-emitting diodes (OLEDs), to a light-emitting layer comprising the inventive fluoranthene derivatives as emitter molecules, to an OLED comprising the inventive light-emitting layer and to devices comprising the inventive OLED.

13 Claims, No Drawings

OTHER PUBLICATIONS

Barret G.C.U-Hoie, N.P. et al., "Carcinogenic Nitrogen Compounds. Part XXV. Steric Hindrance to Cyclisation of 6-Aminochrysene and its Derivatives.", J. Chem. Soc., pp. 2946-2949, 1958.

Campbell, N. et al, "3-Formylfluoranthene and 3,9-diacetylfluoranthene", Chem. Ind., pp. 1114-1115, 1970.

Buu-Hoie, N.P. et al., "Studien im Gebiet der aromatischen kondensierten Keme, XII. Mitteil.): tert-buty-lierung mehrkemiger aromatischer Kohlenwasserstoffe.", Chem. Ber., vol. 77, pp. 121-125, 1944. (with English abstract).

Bernius, Mark T. et al., "Progress with Light-Emitting Poymers", Advanced Materials, vol. 12, No. 23, pp. 1737-1750, 2000.

COMPOUNDS BASED ON FLUORANTHENE AND USE THEREOF

The present invention relates to fluoranthene derivatives, to processes for their preparation and to the use of fluoranthene derivatives as emitter molecules in organic light-emitting diodes (OLEDs), to a light-emitting layer comprising the inventive fluoranthene derivatives as emitter molecules, to an OLED comprising the inventive light-emitting layer and to devices comprising the inventive OLED.

Organic light-emitting diodes (OLEDs) utilize the property of materials of emitting light when they are excited by electrical current. OLEDs are of particular interest as an alternative to cathode ray tubes and liquid-crystal displays for the production of flat visual display units.

Numerous materials which emit light on excitation by electrical current have been proposed.

A review of organic light-emitting diodes is disclosed, for example, in M. T. Bernius et al., Adv. Mat. 2000, 12, 1737. The requirements on the compounds used are high and it is typically not possible to fulfill all demands made with the known materials.

U.S. Pat. No. 5,281,489 discloses OLEDs which may comprise fluorescent materials including 3,4-benzofluoranthene or monomeric unsubstituted fluoranthene. However, monomeric unsubstituted fluoranthene can migrate under the use conditions existing in the OLEDs. The layer of monomeric unsubstituted fluoranthene is unstable, which results in a low lifetime of the diodes.

The use of specific fluoranthene derivatives is disclosed in US 2002/0022151 A1 and EP-A 1 138 745.

EP-A 1 138 745 relates to an OLED which emits reddish light. This OLED comprises an organic layer which has a compound having a fluoranthene skeleton, the fluoranthene skeleton being substituted by at least one amino group or an alkenyl group. According to the description, preference is given to those fluoranthene derivatives which have at least 5, preferably at least 6 fused rings. These compounds emit light of longer wavelength, so that yellow to reddish light can be emitted. The fluoranthene derivatives disclosed in EP-A 1 138 745 preferably bear an amino group to increase the lifetime of the fluoranthene derivatives.

US 2002/0022151 A1 likewise relates to OLEDs which comprise specific fluoranthene compounds as light-emitting material. These fluoranthene compounds have at least one diarylamino group.

It is an object of the present invention to provide compounds which are suitable as emitter molecules in OLEDs, which have a long lifetime and which are highly efficient in OLEDs.

This object is achieved by a fluoranthene derivative of the general formula (I)

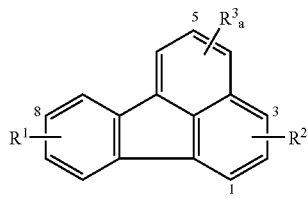

(I)

in which $R^1$, $R^2$, $R^3$ and a are each independently defined as follows:

$R^1$, $R^2$ and $R^3$ are each hydrogen, a linear, branched or cyclic, halogen-, nitro-, ether- or carboxyl-substituted or unsubstituted $C_1$- to $C_{20}$-alkyl group, in which one or more nonadjacent carbon atoms of the alkyl group which is/are not bonded directly to the fluoranthene skeleton may be replaced by Si, P, O or S, a halogen-, nitro-, carboxyl-, alkoxy- or $C_6$- to $C_{14}$-aryl-substituted or unsubstituted $C_6$- to $C_{30}$-aryl group which may be unsubstituted or substituted by linear, branched or cyclic $C_1$- to $C_{20}$-alkyl groups which may be unsubstituted or may in turn be substituted by halogen, nitro, ether or carboxyl groups and/or in which one or more carbon atoms of the alkyl group may be replaced by Si, P, O or S, or a $C_4$- to $C_{14}$-heteroaryl group which is unsubstituted or substituted by the substituents specified with regard to the aryl group and comprises at least one nitrogen or sulfur atom, a group of the formula

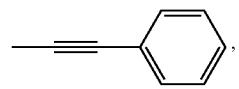

(E)- or (Z)-CH=CH—$C_6R^4{}_5$ in which $R^4$ is H or $CH_3$, a group of the formula or an acryloyl or methacryloyl group, a vinyl ether radical and a group of the formula

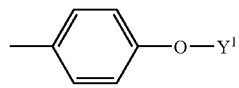

in which $Y^1$ is —CH=$CH_2$, (E)- or (Z)-CH=CH—$C_6H_5$, acryloyl, methacryloyl, methylstyryl, —O—CH=$CH_2$ or glycidyl, a fused aromatic such as naphthalene, anthracene, pyrene, phenanthrene and perylene, which may be substituted by one or more halogen, nitro, ether or carboxyl radical(s), and a is an integer from 0 to 3, with the proviso that at least one of the $R^1$ or $R^2$ radicals is not hydrogen.

The inventive fluoranthene derivatives have substituents which are bonded to the fluoranthene skeleton via a C—C single bond. The inventive fluoranthene derivatives are surprisingly sufficiently stable to be able to be used in a light-emitting layer in OLEDs with a long lifetime. Moreover, the inventive compounds are notable for a very high stability toward photooxidation in the case of use in OLEDs.

$R^1$, $R^2$ and/or $R^3$ may be a linear, branched or cyclic, substituted or unsubstituted $C_1$- to $C_{20}$-, preferably $C_1$- to $C_8$, more preferably $C_1$- to $C_3$-alkyl group. These alkyl groups may be unsubstituted or substituted by halogen, nitro, ether or carboxyl groups. The alkyl groups are more preferably unsubstituted. Moreover, one or more nonadjacent carbon atoms of the alkyl group which is/are not bonded directly to the fluoranthene skeleton may be replaced by Si, P, O or S, preferably by O or S.

In addition, $R^1$, $R^2$ and/or $R^3$ may be $C_6$- to $C_{30}$-, preferably $C_6$- to $C_{14}$-aryl groups, more preferably a $C_6$-aryl group, or $C_4$- to $C_{14}$-, preferably $C_4$- to $C_{10}$-, more preferably $C_4$- to $C_5$-heteroaryl groups comprising at least one nitrogen or sulfur atom. These aryl groups or heteroaryl groups may be unsubstituted or substituted by linear, branched or cyclic $C_1$- to $C_{20}$-, preferably $C_1$- to $C_8$-, more preferably $C_1$- to $C_3$-alkyl groups which may in turn be substituted by halogen, nitro, ether or carboxyl groups. In addition, one or more carbon atoms of the alkyl group may be replaced by Si, P, O or S, preferably O or S. In addition, the aryl groups or the heteroaryl groups may be substituted by halogen, nitro, carboxyl groups or alkoxy groups, or $C_6$- to $C_{14}$-, preferably $C_6$- to $C_{10}$-aryl groups. More preferably, $R^1$, $R^2$ and/or $R^3$ are each $C_6$- to $C_{14}$-aryl groups which are substituted by halogen, preferably Cl or F, or nitro groups. Most preferably, these aryl groups bear from one to three halogen or nitro groups, most preferably one or two halogen or nitro groups. Especially preferred is a $C_6$-aryl group which is substituted by one or two halogen or nitro groups. The substituents of the $C_6$-aryl group are preferably in the 4-position of the aryl group in the case of one substituent, and preferably in the 3- and 5-position in the case of two substituents. Also preferred is a $C_6$-aryl group which is unsubstituted (i.e. a phenyl group). Heteroaryl groups used with preference are unsubstituted. Very particularly preferred heteroaryl groups are thionyl groups or pyridyl groups.

In addition, $R^1$, $R^2$ and/or $R^3$ may be a group of the formula (E)- or (Z)-CH=CH—$C_6R^4{}_5$ in which $R^4$ is H or $CH_3$, a group of the formula

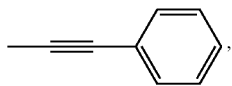

or an acryloyl or methacryloyl group. $R^1$, $R^2$ and/or $R^3$ are preferably each a styryl, acryloyl or methacryloyl group.

$R^1$, $R^2$ and/or $R^3$ may also be a group of the formula

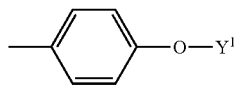

in which $Y^1$ is —CH=$CH_2$, (E)- or (Z)-CH=CH—$C_6H_5$, acryloyl, methacryloyl, methylstyryl, —O—CH=$CH_2$ or glycidyl, or a fused aromatic such as naphthalene, anthracene, pyrene, phenanthrene or perylene, each of which may be substituted by one or more halogen, nitro or carboxyl radical (s).

The $R^1$, $R^2$ and $R^3$ radicals may each independently be selected from the aforementioned radicals with the proviso that at least one of the R or $R^2$ radicals is not hydrogen, i.e. unsubstituted fluoranthene is not encompassed by the inventive compounds. $R^1$, $R^2$ and $R^3$ are most preferably selected from the aforementioned aryl or heteroaryl groups. Particularly preferred aryl or heteroaryl groups have already been mentioned above. Most preferably, $R^1$ and $R^2$ are each independently a $C_6$- to $C_{14}$-aryl group which is unsubstituted or substituted by linear or branched, unsubstituted $C_1$- to $C_8$-alkyl groups, halogen or nitro groups, or a $C_4$- to $C_{10}$-heteroaryl group which is unsubstituted or substituted correspondingly to the aryl group and comprises at least one nitrogen or sulfur atom.

In a further very particularly preferred embodiment, $R^1$ and $R^2$ are each independently a phenyl group which is unsubstituted or substituted by linear or branched, unsubstituted $C_1$- to $C_8$-alkyl groups, halogen or nitro groups and more preferably bears no, one or two substituents, a thiophene radical, a pyrrole radical, a pyridine radical or a pyrimidine radical.

a in the general formula I is an integer from 0 to 3, preferably 0 or 1, most preferably 0, i.e., in a very particularly preferred embodiment, the fluoranthene derivative of the general formula I comprises two substituents, specifically $R^1$ and $R^2$. In a very particularly preferred embodiment, these substituents are arranged in the 3- and the 8-position of the fluoranthene skeleton. In that case, the 3-position is substituted by the $R^2$ radical and the 8-position by the $R^1$ radical. Most preferably, neither $R^1$ nor $R^2$ is hydrogen.

In a very particularly preferred embodiment, the present invention encompasses fluoranthene derivatives which, in the 3- and in the 8-position, bear a phenyl group substituted by one or two substituents or a heteroaryl group selected from a thionyl group and a pyridyl group.

Especially preferred are fluoranthene derivatives which, in the 3- and 8-position, bear a substituted phenyl group, in which case the phenyl group preferably bears one or two substituents. The substituents of the phenyl group have already been mentioned above. Very particularly preferred substituents are halogen groups such as fluorine, chlorine or bromine, preferably fluorine, nitro groups or aromatic groups such as phenyl or biphenyl radicals. When the substituted phenyl group is substituted by a substituent, it is most preferably substituted in the 4'-position of the phenyl radical, i.e. in the p-position to the fluoranthene radical. When the substituted phenyl group is substituted by two substituents, the substitution is most preferably in the 3'- and 5'-position.

It has been found that, surprisingly, fluoranthene derivatives which bear a substituted phenyl group in the 3- and 8-position emit light in the blue region of the visible electromagnetic spectrum.

To produce displays which comprise the colors of the entire visible spectrum, it is necessary to provide OLEDs which emit light in the red region of the visible electromagnetic spectrum, OLEDs which emit light in the green region of the visible electromagnetic spectrum and OLEDs which emit light in the blue region of the visible electromagnetic spectrum. It has been found that especially the provision of efficient OLEDs which emit light in the blue region of the visible electromagnetic spectrum is problematic.

The inventive fluoranthene derivatives which bear a substituted phenyl group in the 3- and 8-position are suitable for producing OLEDs which emit light in the blue region of the visible electromagnetic spectrum.

The inventive fluorahthene derivatives of the general formula I may be prepared by reacting fluoranthene derivatives halogenated, especially brominated, at the positions at which the $R^1$, $R^2$ and, if appropriate, $R^3$ radicals are bonded to the fluoranthene skeleton in the desired fluoranthene derivatives of the general formula I with the boronic acids or boronic esters corresponding to the desired $R^1$, $R^2$ and, if appropriate, $R^3$ radicals under Pd(0) catalysis in the presence of a base (Suzuki coupling). Substitution of fluoranthene derivatives by formation of a carbon-carbon bond by means of Suzuki coupling is not known to date from the prior art.

Instead of the boronic acids or boronic esters corresponding to the desired $R^1$, $R^2$ and, if appropriate, $R^3$ radicals, it is also possible to use other boron compounds which bear the desired $R^1$, $R^2$ and, if appropriate, $R^3$ radicals in the reaction with the halogenated fluoranthene derivatives. The boron compounds are compounds of the general formulae $R^1$—B (O—$[C(R^4)_2]_n$)—O, $R^2$—B(O—$[C(R^4)_2]_n$)—O and, if appropriate, $R^3$—B(O—$[C(R^4)_2]_n$)—O, in which $R^1$, $R^2$ and $R^3$ are each as defined above, $R^4$ is the same or different and is selected from hydrogen or $C_1$-$C_{20}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-decyl, n-dodecyl or n-octadecyl; preferably $C_1$-$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl or n-decyl, more preferably $C_1$-$C_4$-alkyl such as methyl, ethyl, n-propyl, isopropyl, n-butyl, isobutyl, sec-butyl and tert-butyl, most preferably methyl; and n is an integer from 2 to 10, preferably from 2 to 5.

It is likewise possible to carry out the Suzuki coupling by reacting fluoranthene derivatives substituted by boronic acid or boronic ester groups or groups of the formula —B(O—[C($R^4$)$_2$]$_n$)—O at the positions at which the $R^1$, $R^2$ and, if appropriate, $R^3$ radicals are bonded to the fluoranthene skeleton in the desired fluoranthene derivatives with the halides corresponding to the desired $R^1$, $R^2$ and, if appropriate, $R^3$ radicals under Pd(0) catalysis in the presence of a base. $R^4$ is as defined above.

Preference is given to effecting the Suzuki coupling in the embodiment mentioned first.

The boronic acids and boronic esters corresponding to the desired R, $R^2$ and, if appropriate, $R^3$ radicals or the fluoranthene derivatives may be prepared by processes known from the prior art. For example, it is possible to prepare the boronic acids and boronic esters by reacting Grignard or lithium reagents with boranes, diboranes or borates. The other suitable boron compounds are prepared by processes known to those skilled in the art.

The preparation of the halogenated, preferably brominated, fluoranthene derivatives is known to those skilled in the art. For example, a bromination can be effected by reacting fluoranthene with elemental bromine in a solvent, for example chloroform. A process for bromination of fluoranthene derivatives is disclosed, for example, in DE-A 32 09 426. The halides corresponding to the $R^1$, $R^2$ and, if appropriate, $R^3$ radicals are commercially available or obtainable by processes known to those skilled in the art.

Suitable Pd(0) catalysts are all customary Pd(0) catalysts. For example, it is possible to use tris(dibenzylideneacetone)dipalladium(0) or tetrakis(triphenylphosphine)palladium(0). The catalysts are used generally in an amount of from 0.001 to 15 mol %, preferably from 0.01 to 10 mol %, more preferably from 0.1 to 5 mol %, based on the fluoranthene compound.

In the Suzuki coupling, all bases used customarily in the Suzuki coupling may be used. Preference is given to using alkali metal carbonates such as sodium carbonate or potassium carbonate. The base is used generally in a molar excess of from 20 to 200 times, preferably from 20 to 100 times, more preferably from 20 to 80 times, based on the fluoranthene compounds.

The component corresponding to the desired $R^1$, $R^2$ and, if appropriate, $R^3$ radicals (boronic acid, the corresponding boronic ester or the other suitable boron compounds or the corresponding halides) are used in a ratio relative to the halogenated fluoranthene derivative or the fluoranthene derivative substituted by boronic acid or boronic ester groups or groups of the formula —B(O—[C($R^4$)$_2$]$_n$)—O of from 100 to 400 mol %, preferably from 100 to 300 mol %, more preferably from 100 to 150 mol %.

The reaction is effected generally at a temperature of from 40 to 140° C., preferably from 60 to 120° C., more preferably from 80 to 100° C. The pressure is generally standard pressure.

The reaction is generally carried out with exclusion of oxygen. Typically, the reaction is effected in a solvent selected from the group consisting of benzene, toluene, tetrahydrofuran, 1,4-dioxane and petroleum ether.

In a particularly preferred embodiment of the process according to the invention, a halogenated fluoranthene is initially charged in solution under protective gas and admixed with the base which is preferably present in dissolved form, for example in an ethanol/water mixture, and a boronic acid. Thereafter, the Pd(0) catalyst is added under protective gas. The mixture is stirred at the aforementioned temperatures and pressures over a period of generally from 2 to 120 hours, preferably from 4 to 72 hours, more preferably from 6 to 48 hours. Thereafter, the reaction mixture is worked up by processes known to those skilled in the art.

The workup can be effected, for example, by pouring the reaction mixture onto an alcohol, preferably methanol, subsequently filtering and, after drying the filtrate, for example with molecular sieve or $MgSO_4$, concentrating it and purifying it by chromatography.

In addition to the Suzuki coupling, the inventive fluoranthene derivatives may be prepared by other processes known to those skilled in the art, especially other coupling reactions.

In a further embodiment of the present invention, the inventive fluoranthene derivatives of the formula I are obtained by reacting fluoranthene derivatives halogenated, especially brominated, at the positions at which the $R^1$, $R^2$ and, if appropriate, $R^3$ radicals are bonded to the fluoranthene skeleton in the desired fluoranthene derivatives of the general formula I with the bromine compounds corresponding to the desired $R^1$, $R^2$ and, if appropriate, $R^3$ radicals under Ni(0) catalysis (Yamamoto coupling).

Substitution of fluoranthene derivatives by forming a carbon-carbon bond by means of Suzuki coupling or Yamamoto coupling is to date unknown from the prior art.

In a preferred embodiment of the Yamamoto coupling, a solution, preferably a DMF solution, of the catalyst prepared from an Ni(0) compound, preferably Ni(COD)$_2$, and bipyridyl in equimolar amounts is used with exclusion of oxygen. The halogenated, preferably brominated, fluoranthene derivative and the bromine compounds corresponding to the desired $R^1$, $R^2$ and, if appropriate, $R^3$ radicals in a solvent, preferably toluene, are added to this solution with exclusion of oxygen.

The reaction conditions, such as temperature, pressure, solvent, ratio of the fluoranthene component to the component corresponding to $R^1$, $R^2$ and, if appropriate, $R^3$, exclusion of oxygen and workup, in the preparation of the inventive fluoranthene derivatives by means of Yamamoto coupling correspond to those of the Suzuki coupling.

Suitable Ni(0) compounds for preparing the catalyst are all customary Ni(0) compounds. For example, it is possible to use Ni($C_2H_4$)$_3$, Ni(1,5-cyclooctadiene)$_2$ ("Ni(COD)$_2$"), Ni(1,6-cyclodecadiene)$_2$ or Ni(1,5,9-all-trans-cyclododecatriene)$_2$. The catalysts are used generally in an amount of from 1 to 100 mol %, preferably from 5 to 80 mol %, more preferably from 10 to 70 mol %, based on the fluoranthene compound.

The processes according to the invention make it possible to provide a wide range of fluoranthene derivatives which are substituted by means of C—C bond formation. It is thus possible to provide fluoranthene derivatives which fluoresce with the wavelength desired in each case.

The inventive fluoranthene derivatives are notable in that they are suitable for emitting electromagnetic radiation in the blue region of the visible spectrum in organic light-emitting diodes (OLEDs).

The present invention therefore further provides for the use of fluoranthene derivatives of the general formula I as emitter molecules in organic light-emitting diodes (OLEDs). Preferred fluoranthene derivatives and their preparation processes have already been mentioned above.

Organic light-emitting diodes are in principle formed from a plurality of layers. Various layer sequences are possible, for example:
- anode/hole-transporting layer/light-emitting layer/cathode;
- anode/light-emitting layer/electron-transporting layer/cathode;
- anode/hole-transporting layer/light-emitting layer/electron-transporting layer/cathode.

The inventive fluoranthene derivatives of the general formula I are preferably used in the light-emitting layer as emitter molecules. The present invention therefore further provides a light-emitting layer comprising one or more fluoranthene derivatives of the general formula I as emitter molecules. Preferred fluoranthene derivatives have already been mentioned above.

The fluoranthene derivatives may themselves form the light-emitting layer. In the light-emitting layer, customary light-emitting materials, dopants, hole-transporting substances and electron-transporting substances may be used if necessary in addition to the inventive fluoranthene derivatives. However, the fluoranthene derivatives of the general formula I according to the present application may also be used as dopants in the light-emitting layer. Preference is given to adding fluoranthene derivatives of the general formula I to the light-emitting layer in a concentration of from 1 to 70% by weight, preferably from 1 to 20% by weight.

The individual aforementioned layers of the OLED may in turn be formed from two or more layers. For example, the hole-transporting layer may be formed from a layer into which holes are injected from the electrode, referred to hereinafter as hole-injecting layer, and a layer which transports the holes from the hole-injecting layer away into the light-emitting layer. This layer is referred to hereinafter as hole-transporting layer. The electron-transporting layer may likewise consist of a plurality of layers, for example of a layer in which electrons are injected by the electrode, referred to hereinafter as electron-injecting layer, and of a layer which receives electrons from the electron-injecting layer and transports them into the light-emitting layer, referred to hereinbelow as electron-transporting layer. These layers mentioned are each selected according to factors such as energy level, thermal resistance and charge carrier mobility, and also energy difference of the layers mentioned with the organic layers or the metal electrodes. Suitable materials which are used in the light-emitting layer as a base material in combination with the inventive fluoranthene derivatives of the general formula (I) are anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, metal complexes of quinoline, metal complexes of aminoquinoline, metal complexes of benzoquinoline, imines, diphenylethylene, vinylanthracene, diaminocarbazole, pyrane, thiopyrane, polymethine, merocyanine, chelates of oxinoid compounds with imidazoles, quinacridone, rubrene, stilbene derivatives and fluorescent pigments.

The hole-transporting material used is generally a compound which has the ability to take up the holes from the anode, to transport holes, and is simultaneously suitable for injecting holes into the light-emitting layer. Suitable hole-transporting materials are, for example, metal complexes of phthalocyanine, of naphthalocyanine, of porphyrin, pyrazolones, tetrahydroimidazoles, hydrazones, acylhydrazones, polyarylalkanes, thiophenes, tertiary aromatic amines such as triphenylamines of the benzidine type, triphenylamines of the styrylamine type, triphenylamines of the diamine type, derivatives of these compounds, silanamines, especially silanamines which bear triphenylsilyl groups, and macromolecular compounds such as polyvinylcarbazoles, polyvinylsilanes, polythiophene, poly(p-phenylene) and conductive macromolecules. Particularly preferred hole-transporting materials are disclosed, for example, in EP-A 1 138 745 and Chen et al. Macromol. Symp. 125, 9 to 15 (1997).

Suitable electron-transporting materials are compounds which have the ability to transport electrons, and which can themselves inject electrons into the light-emitting layer. Suitable electron-transporting materials are, for example, oxazoles, oxadiazoles, triazoles, imidazoles, imidazolones, imidazolethiones, fluorenone, anthraquinonedimethane, diphenoquinone, thiopyran dioxide, oxazole, oxadiazole, triazole, imidazole, perylenetetracarboxylic acid, fluorenylidenemethane, distyrylarylenes, arylenes, coumarins and derivatives of the compounds mentioned, and also metal chelates. Especially suitable are $AlQ_3$ (tris(8-hydroxyquinolato) aluminum), $BeBq_2$, 1,3,4-oxidazole derivatives (OXDs) such as PBD and 1,2,4-triazoles (TAZs). Additionally suitable are bis(benzimidazolyl) derivatives of peryldenedicarboximide (PD), naphthalenedicarboximide (ND) and thiopyran sulfones (TPS). Electron-transporting materials used with preference are disclosed, for example, in EP-A 1 138 745. In order to increase the stability of the inventive OLED against temperature, moisture and other influences, the OLED can be protected by a protective layer on the surface of the OLED, this protective layer being formed, for example, from a resin or silicone oil.

The conducting material used which is suitable for the anode of the inventive OLED is preferably material which has a work function of $\geq 4$ eV. Suitable materials for the anode are, for example, carbon, vanadium, iron, cobalt, nickel, tungsten, gold, platinum, palladium and alloys of these materials, metal oxides as used for ITO substrates (ITO=indium tin oxide) and NESA substrates, such as tin oxides and indium oxides and organic conducting polymers such as polythiophene and polypyrrole.

A suitable conducting material for the cathode is material which has a work function of $<4$ eV. Materials suitable for the cathode are, for example, magnesium, calcium, tin, lead, titanium, yttrium, lithium, ruthenium, manganese, aluminum and alloys of these materials.

The anode and the cathode may, if appropriate, have a multilayer structure composed of two or more layers.

The OLEDs of the present invention preferably additionally have a layer of a chalcogenide, of a metal halide or of a metal oxide on the surface of at least one electrode pair. Particular preference is given to a layer of a chalcogenide (including an oxide) of a metal, for example silicon or aluminum, applied to the surface of the anode on the side which points in the direction of the light-emitting layer. Preference is given to applying a layer of a metal halide or of a metal oxide to the surface of the cathode which points in the direction of the light-emitting layer. Owing to the two layers mentioned above, the stability of the OLEDs can be improved. Preferred materials for the layers mentioned are specified, for example, in EP-A 1 138 745.

Further preferred embodiments of the individual layers of the OLEDs are likewise detailed in EP-A 1 138 745.

In general, at least one side of the inventive OLED is transparent in the wavelength range in which light is to be emitted in order to enable efficient light emission. The transparent electrode is generally applied by vapor deposition or sputtering. On the light-emitting side of the OLED, the electrode preferably has a transparency for light of ≧10%. Suitable materials are known to those skilled in the art. For example, glass substrates or transparent polymer films may be used.

The preparation of the inventive OLEDs is known to those skilled in the art. It is possible that each layer of the OLED is prepared by a dry process for film formation, such as vapor deposition, sputtering, plasma plating or ion plating, or a wet process of film formation such as spin-coating, dipping or flow-coating. The thickness of the individual layers is not restricted and customary thicknesses are known to those skilled in the art. Suitable thicknesses of the layers are generally in the range from 5 nm to 10 µm. Preference is given to thicknesses of from 10 nm to 0.2 µm. The performance of dry processes or wet processes for film formation is known to those skilled in the art.

The present invention thus provides an OLED comprising a light-emitting layer which comprises one or more fluoranthene derivatives of the general formula (I) as emitter molecules. Preferred compounds of the general formula (I) have already been mentioned above.

The inventive OLED may be used in numerous devices. Thus, the present invention further provides a device selected from the group consisting of stationary visual display units such as visual display units of computers, televisions, visual display units in printers, kitchen appliances, and advertising panels, illuminations, information panels and mobile visual display units such as visual display units in cell phones, laptops, vehicles, and destination displays on buses and trains.

The examples which follow provide additional illustration of the invention.

EXAMPLES

The nomenclature of the fluoranthenes in the context of the present invention is according to the scheme below:

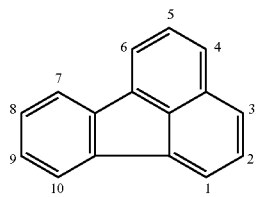

Example 1

38-Di(2-thienyl)fluoranthene

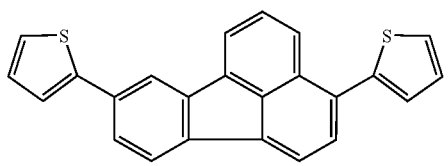

0.1 g of 3,8-dibromofluoranthene, prepared by dibromination of fluoranthene in dimethylformamide (DMF) with bromo-succinimide (NBS), was dissolved under protective gas in 25 ml of dried toluene and degassed repeatedly. 4.9 g of potassium carbonate dissolved in 18 ml of ethanol/water (1:1 parts by volume) and 0.1 g of thiophene-2-boronic acid were added and degassed again. Subsequently, 0.04 g of tetrakis(triphenylphosphine)palladium(0) (Pd(PPh$_3$)$_4$) was added under protective gas and the mixture was stirred at 80° C. for 16 hours. The reaction mixture was poured onto methanol and filtered, and the filtrate was dried with MgSO$_4$ and then concentrated and purified by chromatography on silica gel (Merck Kieselgel 60). Nonpolar impurities were eluted with cyclohexane, the product subsequently with ethyl acetate/cyclohexane (1:50 parts by volume). Yield: 40% as a yellow solid. The structure was confirmed by FD mass spectrometry. In solution (toluene), the compound exhibits yellow-orange fluorescence visible to the eye.

Example 2 bis-3,8-(35-Difluorophenyl)fluoranthene

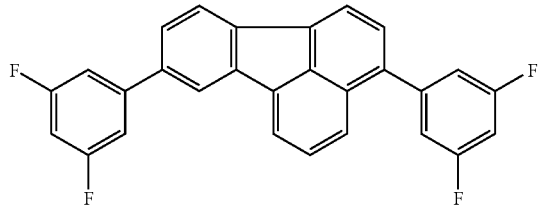

0.5 g of 3,8-dibromofluoranthene, prepared by dibromination of fluoranthene in chloroform with elemental bromine, was dissolved under protective gas in 22 ml of dried toluene and degassed repeatedly. 9.7 g of potassium carbonate dissolved in 28 ml of ethanol/water (1:1 parts by volume) and 0.48 g of 3,5-difluorobenzeneboronic acid were added and degassed again. Subsequently, 0.04 g of tetrakis(triphenylphosphine)palladium(0) (Pd(PPh$_3$)$_4$) was added under protective gas and the mixture was stirred at 80° C. for 16 hours. The reaction mixture was poured onto methanol and filtered, and the filtrate was dried with MgSO$_4$ and then concentrated and purified twice by chromatography on silica gel (Merck Kieselgel 60). Nonpolar impurities were eluted with cyclohexane, the product subsequently with ethyl acetate/cyclohexane (1:50 parts by volume). Yield: 16% as a yellow solid. The structure was confirmed by mass spectrometry (direct evaporation). In solution (toluene), the compound exhibits fluorescence at a wavelength of $\lambda_{max,em}$ (toluene) =468 nm at a quantum yield (toluene) of 43%.

Example 3

3,8-Di(4-nitrophenyl)fluoranthene

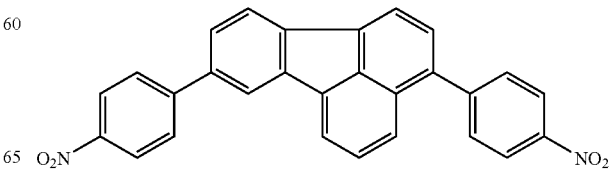

1 g of 3,8-dibromofluoranthene, prepared by dibromination of fluoranthene in chloroform with elemental bromine, was dissolved under protective gas in 43 ml of dried toluene and degassed repeatedly. 19.4 g of potassium carbonate dissolved in 47 ml of ethanol/water (1:1 parts by volume) and 1 g of 4-nitrobenzeneboronic acid were added and degassed again. Subsequently, 0.32 g of tetrakis(triphenylphosphine)palladium(0) (Pd(PPh$_3$)$_4$) was added under protective gas and the mixture was stirred at 80° C. for 16 hours. The reaction mixture was poured onto methanol and filtered, and the filtrate was dried with MgSO$_4$ and then concentrated and purified by chromatography on silica gel (Merck Kieselgel 60). Nonpolar impurities were eluted with cyclohexane, the product subsequently with ethyl acetate/cyclohexane (1:2 parts by volume). Yield: 14% as a yellow solid. The structure was confirmed by mass spectrometry (direct evaporation). In solution (toluene), the compound exhibits fluorescence at a wavelength of $\lambda_{max,em}$ (toluene)=471 nm in a quantum yield (toluene) of 3%.

Example 4

3,8-Bis(biphen-4-yl)fluoranthene

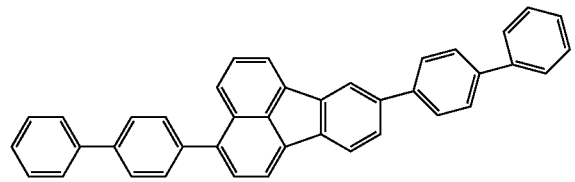

1 g of 3,8-dibromofluoranthene, prepared by dibromination of fluoranthene in chloroform with elemental bromine, was dissolved under protective gas in 100 ml of dried toluene and degassed repeatedly. 19.4 g of potassium carbonate dissolved in 47 ml of ethanol/water (1:1 parts by volume) and 1 g of 4-biphenylboronic acid were added and degassed again. Subsequently, 0.32 g of tetrakis(triphenylphosphine)palladium (0) (Pd(PPh$_3$)$_4$) was added under protective gas and the mixture was stirred at 80° C. for 16 hours. The reaction mixture was filtered and dried. Yield: 14% as a yellowish solid. $\lambda_{max,em}$ (toluene)=479 nm, quantum yield (toluene): 74%.

What is claimed is:

1. An OLED comprising as emitter molecules fluoranthene derivatives of the general formula (I)

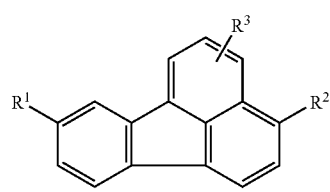

wherein R$^1$ and R$^2$ are each independently selected from
a linear, branched or cyclic, halogen-, nitro-, ether- or carboxyl-substituted or unsubstituted C$_1$- to C$_{20}$-alkyl group, in which one or more nonadjacent carbon atoms of the alkyl group which is/are not bonded directly to the fluoranthene skeleton may be replaced by Si, P, O or S,
a C$_6$- to C$_{30}$-aryl group which may be unsubstituted or substituted by alkoxy-, C$_6$- to C$_{14}$-aryl groups, or linear, branched or cyclic C$_1$- to C$_{20}$-alkyl groups which may be unsubstituted or may in turn be substituted by halogen, nitro, ether or carboxyl groups and/or in which one or more carbon atoms of the alkyl groups may be replaced by Si, P, O or S, or a C$_4$- to C$_{14}$-heteroaryl group which is unsubstituted or substituted by the substituents specified with regard to the aryl group and comprises at least one nitrogen or sulfur atom,
a group of the formula (E)- or (Z)-CH=CH—C$_6$R$^4_5$ in which R$^4$ is H or CH$_3$, a group of the formula

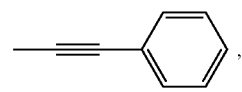

an acryloyl or methacryloyl group, a vinyl ether radical or a group of the formula

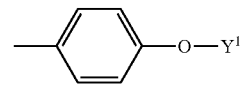

in which Y$^1$ is —CH=CH$_2$, (E)- or (Z)- CH=CH—C$_6$H$_5$, acryloyl, methacryloyl, methylstyryl, —O—CH=CH$_2$ or glycidyl, and
a fused aromatic such as naphthalene, anthracene, pyrene, phenanthrene and perylene, which may be substituted by one or more halogen, nitro, ether or carboxyl radicals, and wherein R$^3$ is hydrogen.

2. The OLED according to claim 1, wherein R$^1$ and R$^2$ in the fluoranthene derivatives are each independently a C$_6$- to C$_{14}$-aryl group which is unsubstituted or substituted by linear or branched, unsubstituted C$_1$- to C$_8$-alkyl groups, halogen or nitro groups, or a C$_4$- to C$_{10}$-heteroaryl group which is unsubstituted or substituted correspondingly to the aryl group and comprises at least one nitrogen or sulfur atom.

3. The OLED according to claim 2, wherein R$^1$ and R$^2$ in the fluoranthene derivatives are each independently a phenyl group which is unsubstituted or substituted by linear or branched, unsubstituted C$_1$- to C$_8$-alkyl groups, halogen or nitro groups, a thiophene radical, a pyrrole radical, a pyridine radical or a pyrimidine radical.

4. The OLED according to claim 3, wherein R$^1$ and R$^2$ in the fluoranthene derivatives are each independently a phenyl group which bears no, one or two substituents.

5. A light-emitting layer comprising one or more fluoranthene derivatives of the general formula (I) as defined in claim 1 as emitter molecules.

6. An OLED comprising a light-emitting layer according to claim 5.

7. A device selected from the group consisting of stationary visual display units such as visual display units of computers, televisions, visual display units in printers, kitchen appliances, and advertising panels, illuminations, information panels and mobile visual display units such as visual display units in cell phones, laptops, vehicles, and destination displays on buses and trains, comprising an OLED according to claim 6.

8. An OLED comprising as emitter molecules fluoranthene derivatives of the following general formula (I):

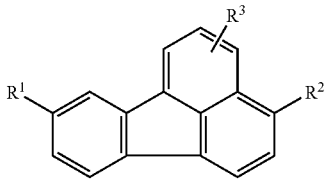
(I)

wherein $R^1$ and $R^2$ are each independently selected from:
- a $C_6$- to $C_{14}$-aryl group which is unsubstituted or substituted by linear or branched, unsubstituted $C_1$- to $C_8$-alkyl groups, halogen or nitro groups; and
- a $C_4$- to $C_{10}$-heteroaryl group which is unsubstituted or substituted by linear or branched, unsubstituted $C_1$- to $C_8$-alkyl groups, halogen or nitro groups, and comprises at least one nitrogen or sulfur atom; and wherein $R^3$ is hydrogen.

9. The OLED according to claim 8, wherein $R^1$ and $R^2$ are each independently selected from a phenyl group which is unsubstituted or substituted by linear or branched, unsubstituted $C_1$- to $C_8$-alkyl groups, halogen or nitro groups, a thiophene radical, a pyrrole radical, a pyridine radical or a pyrimidine radical.

10. The OLED according to claim 9, wherein $R^1$ and $R^2$ are each independently selected from a phenyl group which bears no, one or two substituents.

11. A light-emitting layer comprising as emitter molecules one or more fluoranthene derivatives of the general formula (I) according to claim 8.

12. An OLED comprising the light-emitting layer according to claim 11.

13. A device comprising the OLED according to claim 12, wherein the device is selected from stationary visual display units, visual display units in computers, visual display units in televisions, visual display units in printers, visual display units in kitchen appliances, visual display units in advertising panels, visual display units in illuminations, visual display units in information panels, mobile visual display units, visual display units in cell phones, visual display units in laptops, visual display units in vehicles, destination displays on buses and destination displays on trains.

* * * * *